United States Patent
Strauss, III et al.

(10) Patent No.: US 7,807,366 B2
(45) Date of Patent: Oct. 5, 2010

(54) GENETIC MARKERS FOR ASSESSING RISK OF PREMATURE BIRTH RESULTING FROM PRETERM PREMATURE RUPTURE OF MEMBRANES

(75) Inventors: Jerome F. Strauss, III, Richmond, VA (US); Hongyan Wang, Shanghai (CN)

(73) Assignee: Virginia Commonwealth University, Richmond, VA (US)

( * ) Notice: Subject to any disclaimer, the term of this patent is extended or adjusted under 35 U.S.C. 154(b) by 607 days.

(21) Appl. No.: 11/734,383

(22) Filed: Apr. 12, 2007

(65) Prior Publication Data

US 2008/0254454 A1    Oct. 16, 2008

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6; 435/91.2; 536/23.1; 536/24.3

(58) Field of Classification Search ........................ None
See application file for complete search history.

(56) References Cited

U.S. PATENT DOCUMENTS 5,698,404 A * 12/1997 Strauss et al. ................ 435/7.4

OTHER PUBLICATIONS

Wang et al; J Soc. Gynecol. Investig. vol. 12, p. 285A; Feb. 2005.*
Wang et al; PNAS vol. 103, pp. 13463-13467, Sep. 5, 2006.*

* cited by examiner

*Primary Examiner*—Jehanne S Sitton
(74) *Attorney, Agent, or Firm*—Whitham, Curtis, Christofferson & Cook, P.C

(57) ABSTRACT

A method to identify women who are at risk for preterm delivery due to premature rupture of membranes (PPROM) is provided. The method entails detecting the presence of SERPINH1 gene variants that express low levels of the gene product, heat shock protein Hsp47. The occurrence of a T (rather than C) at a single nucleotide polymorphism (SNP) site at position −656 of the SERPINH1 gene promoter, together with the absence of a 12 base pair deletion at positions −694 to −683 of the promoter, result in an increased risk of PPROM. The method enables medical professionals to identify those at risk, and to provide suitable therapeutic intervention.

4 Claims, 4 Drawing Sheets

```
accaccaccaggcttccccacaaccactaacagagggcagggacccaggtgattgactcatttgc
tgggtactgggattttttgctccccaggatccaggcaagcacctagaagaaagaagatactcaa
tgcattcattcatgactgaatgaatgaagagtccctaccctgtcccttcctctccatactgcgtc
catccaatagctatcattaaactactaaagaggacttttcggagggtagggagcctcggctgatc
agaaattgagccactgtcgcccagattatttagggttcctaaataatctgcctcactgaatcac
tgaattccctactaacaggtacataccccacagatggacatcgcacagggcaaggactttgttca
gctctcagctgtgtcctcagcacctagaacagtaatgaatacctagcttaacttggaggtcaag
gagctatcagtttgcgagggtggggtaggaattgacagtgagacctgaggcctgtgggagggac
ccaaagagggagggatgcaatagggaggggccaggggtgacaaggattgaggaagggagagag
gggggaaaaaaagcaagggatgccttagaaccacatttcacagccaagggaacagaggcccagaa
agggaaagtaacctgcttagggtcacacagcaccttgctcagtggagagccaggttttccttcct
gtgcactcctccaagcccagccagaccacctgaagttccccaggcatctctgcctctattactc
cacgacttgaactttccgggtgccgggcaggtaccgggtctggtctgctccctctccctctggcc
atcgctgaggttgaggttttttgaatgtacaagtatggagaagggcactgccttcagaagcctga
acgtctcccctgagagggagggggtgcacaggactcaattgtttcagcttgaaaatgggggagag
cggggagaagggagatggctctgcttggggcagagcccctgcggggaaagggcgcctgaaagg
acgtgcgattcggagtgggctagcttatgcagagagcctgggggtgggaggaagctcgcactctg
aaggacacgctgatccccgtggggactcccggcgcccgcagcccgggccgccgagggaggcagt
aggacccaggggccgggaggcgccggcagagggaggggccgggggccggggaggttttgagggag
gtctttggcttttttggcggagctgggcgccctccggaagcgtttccaactttccagaagttt
ctcgggacgggcaggagggggtggggactgccatatatagatcccgggagcaggggagcgggcta
agagtagaatc
```

*Figure 1*

GENETIC MARKERS FOR ASSESSING RISK OF PREMATURE BIRTH RESULTING FROM PRETERM PREMATURE RUPTURE OF MEMBRANES

This invention was made using funds from grants from the National Institutes of Health having grant number HD 34612. The United States government may have certain rights in this invention.

BACKGROUND OF THE INVENTION

1. Field of the Invention

The invention generally relates to assessing the level of risk a person has or may have for preterm delivery due to preterm premature rupture of membranes (PPROM). In particular, the invention provides a method to assess the level of risk for preterm delivery due to PPROM by detecting SERPINH1 gene variants that express low levels of the gene product, heat shock protein Hsp47. The method can be used to help advise patients that are pregnant or that are planning a pregnancy, as well as to advise prospective parents regarding chances that their child may be born prematurely as a result of PPROM.

2. Background of the Invention

Prematurity is a major problem in the United States, costing the health care system more than 26 billion dollars each year for the care of premature infants. Long-term disabilities associated with prematurity add additional costs. There are significant racial/ethnic disparities in the incidence of prematurity, with African-American women experiencing a disproportionate number of preterm births (2 to 3-fold more) compared to European-American women (1, 2). This disparity cannot be explained by socioeconomic status or access to health care (3). Several factors are thought to contribute to premature birth including infection, decidual bleeding/hemorrhage, stress, lifestyle (e.g., smoking, illicit drug use) and genetics. There is emerging evidence suggesting that interactions among these factors (i.e., gene-environment interactions) can increase the likelihood of a preterm birth (4, 5).

The prior art has thus far failed to provide a genetic method to identify women who are at risk for preterm delivery due to PPROM, particularly women of African-American descent, who are particularly prone to preterm delivery.

SUMMARY OF THE INVENTION

One approach to the elucidation of the ethnic disparity in risk for prematurity is to identify genetic variants with different allele frequencies among populations that are associated or linked to this outcome. Knowledge of such a genotype could be used to identify subjects who might benefit from therapeutic interventions. This would allow preventative measures (e.g., lifestyle change or medical therapy) to be instituted prior to the onset of preterm labor. It could also facilitate clinical trials of prevention therapies.

Preterm births cluster in families, and the strongest predictor of a preterm birth is a prior preterm delivery (6, 7). The notion that genetic factors, particularly genes involved in collagen metabolism, play a role in preterm birth is supported by the frequent occurrence of preterm birth after premature preterm rupture of membranes (PPROM) when the fetus is affected with Ehlers-Danlos syndrome (8). The amount of fibrillar collagen laid down in the amnion gives the fetal membranes tensile strength, and PPROM fetal membranes have reduced collagen content, which could be the result of reduced synthesis or increased catabolism of collagen (13, 14). Candidate gene studies revealed that polymorphisms that increase the promoter activity of genes encoding matrix metalloproteinases, enzymes that break down collagen, are associated with risk of PPROM, the leading identifiable cause of preterm delivery (9-11). Although these studies support the idea that genetic variation contributes to preterm delivery, none of the known variants can account for why African-Americans are at greater risk.

The present invention supplies a solution to this problem by providing a method of identifying women who are at risk for preterm delivery caused by PPROM. The method involves detecting variants of the SERPINH1 gene that express low levels of the gene product (Hsp47). In one embodiment of the invention, the variant is a single nucleotide polymorphism (SNP) at position −656 of the SERPINH1 gene. It has been discovered that a T at position −656 is indicative of a significantly higher risk of PPROM preterm delivery than when a C is at position −656. However, this tendency can be off-set by the presence of a 12-base pair deletion at positions −694 to −683 in the same promoter. If the 12 base-pair deletion is present in a subject with a T at position −656, the risk of preterm delivery is normal. However, if the 12 base-pair deletion is not present in a subject with a T at position −656, the risk of preterm delivery is significantly higher than normal. While this connection between genotype and PPROM was discovered in women of African-American heritage, the methods of the invention are applicable to the screening and determination of risk level in all ethnic groups. The ability to detect the at risk genotype (T at position −656 and no compensating 12 base pair deletion at positions −694 to −683), as described herein, enables health care workers to provide therapeutic interventions (e.g. lifestyle changes, medical therapy, etc.) prior to the onset of preterm labor. In addition, clinical trials of prevention therapies are facilitated by the discovery disclosed herein. Furthermore, prospective parents can be advised about the risks that their child might be born prematurely as a result of PPROM.

The invention provides a method for predicting a risk of preterm delivery. The method comprises the step of detecting, in at least one nucleic acid sample, one or more polymorphisms in a SERPINH1 gene promoter, the one or more polymorphisms being associated with the risk of preterm delivery. In one embodiment of the invention, the one or more polymorphisms in the SERPINH1 gene promoter modulate the level of transcription of the SERPINH1 gene. In one embodiment, the polymorphism is a single nucleotide polymorphism (SNP) at position −656 of the SERPINH1 gene promoter, where the SNP is cytosine (C) or thymine (T). In another embodiment, the polymorphism is a 12-base pair deletion at positions −694 to −683 of the SERPINH1 gene promoter. The two variants may be detected simultaneously. According to the method: i) detection of a T at the single nucleotide polymorphism (SNP) at position −656 of the SERPINH1 gene promoter, without the 12-base pair deletion at positions −694 to −683 of the SERPINH1 gene promoter, is associated with an increased risk of preterm delivery; ii) detection of a T at the single nucleotide polymorphism (SNP) at position −656 of the SERPINH1 gene promoter with the 12-base pair deletion at positions −694 to −683 of the SERPINH1 gene promoter, is not associated with an increased risk of preterm delivery; and iii) detection of a C at the single nucleotide polymorphism (SNP) at position −656 of the SERPINH1 gene promoter, without or with the 12-base pair deletion at positions −694 to −683 of the SERPINH1 gene promoter, is not associated with an increased risk of preterm delivery. In one embodiment of the invention, the one or more nucleic acid samples is a maternal DNA sample or a paternal DNA sample, or both. In another embodiment, the one or more nucleic acid samples is a fetal DNA sample.

The invention also provides a method for decreasing a risk of preterm delivery. The method comprises the steps of 1) obtaining one or more maternal, paternal or fetal nucleic acid samples; 2) detecting in the one or more nucleic acid samples i) a T at a single nucleotide polymorphism (SNP) at position −656 of the SERPINH1 gene promoter, and ii) a 12-base pair deletion at positions −694 to −683 of the SERPINH1 gene promoter; and 3) providing therapeutic intervention to decrease the risk of preterm delivery. In one embodiment of the invention, the therapeutic intervention is, for example, drug therapy, lifestyle changes and/or dietary modifications.

In yet another embodiment, the invention provides a kit comprising 1) oligonucleotides specific for identifying i) a nucleotide at position −656 of a SERPINH1 gene promoter in a nucleic acid sample; and ii) a 12-base pair deletion at positions −694 to −683 of the SERPINH1 gene promoter in a nucleic acid sample; and 2) reagents for carrying out a procedure that uses the oligonucleotides to identify the nucleotide at position −656 of the SERPINH1 gene promoter and the 12-base pair deletion at positions −694 to −683 of the SERPINH1 gene promoter in the nucleic acid sample.

BRIEF DESCRIPTION OF THE DRAWINGS

FIG. 1. Sequence of SERPINH1 (SEQ ID NO: 19) showing the variable SNP (C/T) at position −656 (in bold and indicated by an arrow) and the site of the 12-base pair deletion at positions −694 to −683 (underlined).

DETAILED DESCRIPTION OF THE PREFERRED EMBODIMENTS OF THE INVENTION

Figure 2A:
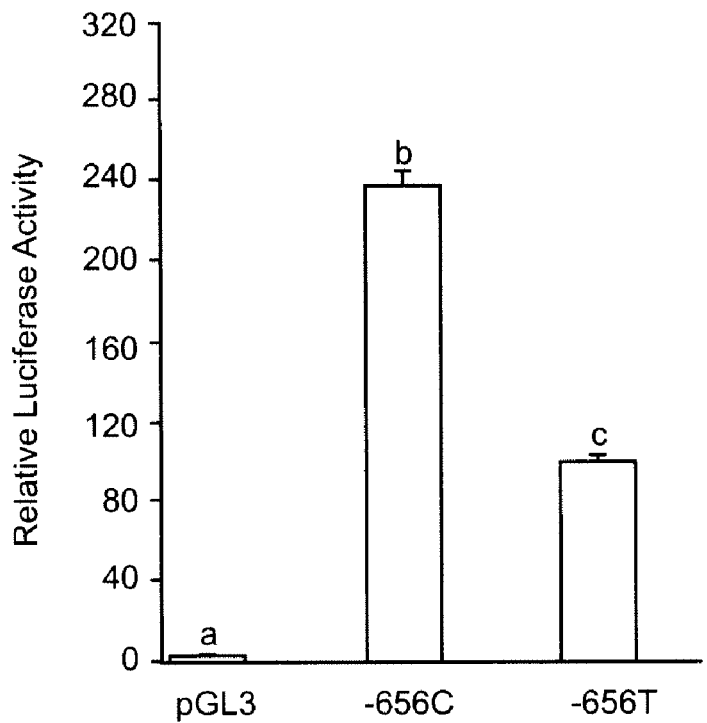
FIG. 2A-C. Effect of the −656 SERPINH1 SNP on promoter activity. SERPINH1 promoter fragments representing the −656 "C" and "T" alleles were cloned into the pGL3 basic vector. The relative *Photinus* luciferase activities±SE (n=3 separate experiments performed with triplicate wells for each cell host, standardized to *Renilla* luciferase) were compared using Tukey-Kramer test. Values with different letters are significantly different (P<0.05) from each other within each cell host. A, anmion fibroblasts; B, dermal fibroblasts; C, uterine smooth muscle cells.

The SERPINH1 gene encodes heat shock protein Hsp47. Hsp47 is localized to the endoplasmic reticulum and serves as a chaperone stabilizing the collagen triple helix. Hsp47 appears to be essential for collagen synthesis and mutant mice lacking Hsp47 die before birth with ruptured blood vessels and a marked reduction in type I collagen. There is a direct relationship between Hsp47 expression and collagen production; type I procollagen increases in proportion to the increase in Hsp 47 levels (12). Rocnik et al. identified a functional SNP in the promoter of the SERPINH1 gene (−656 C/T) and reported that the "T" allele is highly enriched in persons of African ancestry (12).

The present invention is based on the discovery of a link between the SERPINH1 genotype of subjects of African-American heritage and their propensity to experience PPROM. It has been discovered that women carrying fetuses with a T allele (rather than a C allele) at position −656 of the promoter region of the SERPINH1 have an increased risk of PPROM. However, it has also been discovered that this risk increase is nullified if a second polymorphism in the same gene is also present, namely a 12 bp deletion of nucleotides −694 to −683. The presence of the 12 bp deletion results in a reversal of the effect of and/or affords protection against the presence of the T allele, and is equated to a normal level of PPROM risk. In other words, the presence of the T allele is an indicator of increased risk of PPROM unless the 12 bp deletion of nucleotides −694 to −683 is also present.

The invention provides methods for genetically screening parental and/or fetal cells for these two SERPINH1 polymorphisms, thereby identifying women who are likely to be at risk for experiencing PPROM (i.e. those carrying or likely to carry fetuses with the −656 T allele without the compensating 12 bp deletion). Such information allows informed decision making by potential parents prior to or during pregnancy, and/or the opportunity for therapeutic intervention during pregnancy to prevent or decrease the incidence of PPROM in at-risk populations. The sequence of the SERPINH1 promoter region is shown in FIG. 1, and the locations of the SNP at position −656 and the site of the −694 to −683 12 bp deletion are indicated.

Without being bound by theory, the decrease in collagen production that occurs in fetuses carrying the T allele at position −656 without the compensating 12 bp deletion may be responsible for premature rupture of the fetal membranes. The ability to detect the T allele (or other similar variants that cause decreased expression of Hsp47) in a subject's genotype, as described herein, enables health care workers to identify women at risk for premature delivery due to PPROM, and to provide therapeutic interventions (e.g. lifestyle change, medical therapy, etc.) prior to the onset of preterm labor. In addition, clinical trials of prevention therapies are facilitated by the discovery disclosed herein.

While the correlation between genetic variants of the SERPINH1 promoter and the occurrence of preterm delivery due to PPROM was discovered based on the incidence in women of African-American descent, those of skill in the art will recognize that the methods of the invention are not limited to the identification of at-risk women of African-American descent. At risk women of any ethnic background may be successfully identified using the methods of the invention. Further, while the initial discovery was of an SNP at position −656, those of skill in the art will recognize that other variants of the SERPINH1 gene may also be used in a similar manner. For example, other variations in the promoter region or other regulatory regions may cause decreased gene expression; or variations that result in changes in the amino acid sequence of the Hsp47 protein may cause the protein to function at a decreased level, resulting in lower levels of collagen production. All such variants are intended to be encompassed by the present invention.

Examples of those who will benefit from the practice of the invention include women who are contemplating pregnancy and those who are already pregnant, particularly those in the early stages of pregnancy. In one embodiment of the invention, the determination of the risk of PPROM is made by genotyping maternal and/or paternal biological samples (preferably both maternal and paternal samples) either prior to pregnancy, or during pregnancy. By establishing the genotypes of the father and mother, it is possible to estimate the likelihood that the fetus will carry the risk allele. Alternatively, if the genotyping is performed after the onset of pregnancy, fetal cells may be tested directly. Fetal cells include any cells produce by the fetus and which carry the fetal genotype, e.g. cells from the fetus itself, cells sloughed from the fetus, placental cells, etc. Fetal cells may be obtained according to any established method, e.g. by amniocentesis, or isolated from maternal peripheral blood If such testing is carried out after the onset of pregnancy, the screening/testing methods of the invention are preferably carried out as early as possible after pregnancy is diagnosed, for example, preferably within the first trimester. Such an assessment permits a suitable response to the result to be undertaken as early as possible. However, if testing does not occur during the earliest window of opportunity, it can be carried out at a later time, for example, at any time up until delivery. In addition, use of the test is not limited to pregnant women. Any female of child-bearing age may wish to know whether she is likely to be at risk for a pregnancy complicated by PPROM, whether or not she is already pregnant, and particularly if she is contemplating having a child. Further, the test may be of utility for other individuals (e.g. potential fathers) who wish to know if they carry a variant allele and thus are likely to pass it to progeny, or for other reasons. Further, since the product of the SERPINH1 gene is generally involved in collagen production, the presence of a variant allele may also be indicative of other conditions related to insufficient collagen production, such as fibrotic disorders including but not limited to keloids and uterine fibroid tumors. And conversely, as shown in the Examples section below, this variant may contribute to the overproduction of collagen in some cell types (e.g. dermal fibroblasts and uterine smooth muscle cells) and may thus be associated with higher risks of conditions such as keloids (a fibrotic response in skin) and uterine fibroid tumors. Thus, any individual, male or female, of any age, may benefit from knowing their SERPINH1 genotype, and may benefit from the practice of the detection methods of the present invention. Determination of the SERPINH1 genotype may also have forensic or other investigative or identification applications.

In addition, determination of the genotype of the SERPINH1 gene need not be carried out alone. The invention also comprehends the detection and analysis of the genotype of one or more other genes of interest together with the SERPINH1 gene, i.e. identification of the SERPINH1 variants may be included as part of a panel of genes to be analyzed in any of the various genetic profiling methods that are known or under development.

In order to carry out the methods of the invention, a suitable biological sample is obtained, and the genotype of the SERPINH1 gene in the sample is determined. Those of skill in the art will recognize that procedures for obtaining suitable biological samples and for carrying out genotyping of such samples are well-established. Suitable biological samples include but are not limited to blood, serum, urine, swabs e.g. of mucosal cells, amniotic fluid, etc. Any biological sample that may contain DNA sufficiently intact to undergo genotyping procedures may be utilized.

The procedures for establishing the genotype of an individual are well known in the art, and are constantly being refined. See, for example, the descriptions given in U.S. Pat. No. 6,872,533 to Toland et al., (the complete contents of which is hereby incorporated by reference). Numerous methods are known in the art for determining the nucleotide occurrence for a particular variant, (e.g. an SNP or deletion) in a sample. Such methods can utilize one or more oligonucleotide probes or primers, including, for example, an amplification primer pair that selectively hybridizes to a target polynucleotide containing one or more SNPs or deletions. Oligonucleotide probes useful in practicing a method of the invention include, for example, an oligonucleotide that is complementary to and spans a portion of the target polynucleotide, including the position of the SNP and/or deletion, wherein the presence or absence of specific nucleotides at the position(s) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the positions of interest is complementary to the corresponding nucleotide of the probe.

An oligonucleotide ligation assay also can be used to identify a nucleotide occurrence at a polymorphic position, wherein a pair of probes that selectively hybridize upstream and adjacent to and downstream and adjacent to the site of an SNP or deletion, and wherein one of the probes includes a terminal nucleotide complementary to a nucleotide occurrence of the SNP or deletion. Where the terminal nucleotide of the probe is complementary to the nucleotide occurrence, selective hybridization includes the terminal nucleotide such that, in the presence of a ligase, the upstream and downstream oligonucleotides are ligated. As such, the presence or absence of a ligation product is indicative of the nucleotide occurrence at the SNP or deletion site.

An oligonucleotide also can be useful as a primer, for example, for a primer extension reaction, wherein the product (or absence of a product) of the extension reaction is indicative of the nucleotide occurrence. In addition, a primer pair useful for amplifying a portion of the target polynucleotide including the SNP or deletion site can be useful, wherein the amplification product is examined to determine the nucleotide occurrence at the SNP or deletion site. Particularly useful methods include those that are readily adaptable to a high throughput format, to a multiplex format, or to both. The primer extension or amplification product can be detected directly or indirectly and/or can be sequenced using various methods known in the art. Amplification products which span a locus can be sequenced using traditional sequence methodologies (e.g., the "dideoxy-mediated chain termination method," also known as the "Sanger Method" (Sanger, F., et al., J. Molec. Biol. 94:441 (1975); Prober et al. Science 238: 336-340 (1987)) and the "chemical degradation method," "also known as the "Maxam-Gilbert method" (Maxam, A. M., et al., Proc. Natl. Acad. Sci. (U.S.A.) 74:560 (1977)), both references herein incorporated by reference) to determine the nucleotide occurrence at a locus of interest.

Methods of the invention can identify nucleotide occurrences at SNPs and/or deletions using a "microsequencing" method. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at a SNP loci are discussed in Boyce-Jacino, et al., U.S. Pat. No. 6,294,336, incorporated herein by reference, and summarized herein.

Microsequencing methods include the Genetic Bit Analysis™ method disclosed by Goelet, P. et al. (WO 92/15712, herein incorporated by reference). Additional, primer-guided, nucleotide incorporation procedures for assaying polymorphic sites in DNA have also been described (Komher, J. S. et al, Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al, Hum. Mutat. 1:159-164 (1992); Ugozzoli, L. et al., GATA 9:107-112 (1992); Nyren, P. et al., Anal. Biochem. 208:171-175 (1993); and Wallace, WO89/10414). These methods differ from Genetic Bit™ analysis in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al. Amer. J. Hum. Genet. 52:46-59 (1993)).

Alternative microsequencing methods have been provided by Mundy, C. R. (U.S. Pat. No. 4,656,127, incorporated herein by reference) and Cohen, D. et al (French Patent 2,650, 840; PCT Appln. No. WO91/02087) which discusses a solution-based method for determining the identity of the nucleotide of a polymorphic site. As in the Mundy method of U.S. Pat. No. 4,656,127, a primer is employed that is complementary to allelic sequences immediately 3'-to a polymorphic site.

In response to the difficulties encountered in employing gel electrophoresis to analyze sequences, alternative methods for microsequencing have been developed. Macevicz (U.S. Pat. No. 5,002,867, incorporated herein by reference), for example, describes a method for determining nucleic acid sequence via hybridization with multiple mixtures of oligonucleotide probes. In accordance with such method, the sequence of a target polynucleotide is determined by permitting the target to sequentially hybridize with sets of probes having an invariant nucleotide at one position, and a variant nucleotides at other positions. The Macevicz method determines the nucleotide sequence of the target by hybridizing the target with a set of probes, and then determining the number of sites that at least one member of the set is capable of hybridizing to the target (i.e., the number of "matches"). This procedure is repeated until each member of a sets of probes has been tested.

Boyce-Jacino, et al., U.S. Pat. No. 6,294,336 (incorporated herein by reference) provides a solid phase sequencing method for determining the sequence of nucleic acid molecules (either DNA or RNA) by utilizing a primer that selectively binds a polynucleotide target at a site wherein the SNP or deletion is the most 3' nucleotide selectively bound to the target.

In one particular commercial example of a method that can be used to identify a nucleotide occurrence of one or more SNPs in a sample can be determined using the SNP-IT™ method (Orchid BioSciences, Inc., Princeton, N.J.). In general, SNP-IT™ is a 3-step primer extension reaction. In the first step a target polynucleotide is isolated from a sample by hybridization to a capture primer, which provides a first level of specificity. In a second step the capture primer is extended from a terminating nucleotide trisphosphate at the target SNP site, which provides a second level of specificity. In a third step, the extended nucleotide trisphosphate can be detected using a variety of known formats, including: direct fluorescence, indirect fluorescence, an indirect calorimetric assay, mass spectrometry, fluorescence polarization, etc. Reactions can be processed in 384 well format in an automated format using a SNPstream™ instrument (Orchid BioSciences, Inc., Princeton, N.J.).

In another embodiment, a method of the present invention can be performed by amplifying a polynucleotide region that includes an SNP and/or deletion, capturing the amplified product in an allele specific manner in individual wells of a microtiter plate, and detecting the captured target allele.

In a non-limiting example of a method for identifying a nucleotide occurrence at an SNP or deletion mutant, a primer pair is synthesized that comprises a forward primer that hybridizes to a sequence 5' to the SNP or deletion corresponding to this marker and a reverse primer that hybridizes to the opposite strand of a sequence 3' to the SNP or deletion. This primer pair is used to amplify a target polynucleotide that includes the SNP or deletion, to generate an amplification product. A third primer can then be used as a substrate for a primer extension reaction. The third primer can bind to the amplification product such that the 3' nucleotide of the third primer (e.g., adenosine) binds to the SNP or deletion site and is used for a primer extension reaction. The primer can be designed and conditions determined such that the primer extension reaction proceeds only if the 3' nucleotide of the third primer is complementary to the nucleotide occurrence at the SNP or deletion. For example, the third primer can be designed such that the primer extension reaction will proceed if the nucleotide occurrence for the SNP is an thymidine, for example, but not if the nucleotide occurrence of the marker is a cytosine, or vice versa.

Accordingly, using the methods described above, the nucleotide occurrence of a SNP or a deletion can be identified using, for example, an amplification reaction, a primer extension reaction, or an immunoassay. The nucleotide occurrence of the SNP or deletion can also be identified by contacting polynucleotides in the sample or polynucleotides derived from the sample, with a specific binding pair member that selectively hybridizes to a polynucleotide region comprising the a nucleotide occurrence of a SNP or deletion, under conditions wherein the binding pair member specifically binds at or near the SNP or deletion. The specific binding pair member can be an antibody or a polynucleotide.

In one embodiment of the invention, the SNP and deletion are detected using separate sets of primers, one set of which is specific for the SNP and one set of which is specific for the deletion. In another embodiment, both the SNP and the presence or absence of the deletion are detected using a single primer set which flanks both the site of the SNP and the site of the deletion. The design, synthesis and use of such primers, as well as the interpretation of the results of genotyping reactions using such primers, is well known to those of skill in the art.

Women who are identified as carrying a variant such as the T allele at position −656 of the SERPINH1 gene without the compensating 12 bp deletion at positions −694 to −683, and women who are or who become pregnant are candidates for therapeutic intervention to prevent or delay the onset of PPROM. Such types of therapeutic intervention include but are not limited to drug therapies such as drugs that inhibit collagen breakdown (e.g. matrix metalloproteinase (MMP) inhibitors, for example, as described in U.S. Pat. No. 5,698, 404 to Strauss et al., the complete contents of which are hereby incorporated by reference); lifestyle changes (e.g. smoking cessation); dietary modifications such as including dietary supplements (e.g. vitamin C, etc.). Alternatively, even if the baby is delivered early, the knowledge that preterm delivery is possible or likely permits the mother, her support system, and health care workers to prepare for this eventuality, and provide suitable care for the premature infant and mother.

The present invention also provides a kit for diagnosing a predisposition to preterm delivery due to PPROM. The kit includes primers for the detection of the occurrence of a SERPINH1 gene variants such as at position −656, as well as the presence or absence of the 12 bp deletion at positions −694 to −683. The kit may also include primers for the detection of other genetic sequences of interest, e.g. other SNPs, other gene deletions, additions, mutations, etc., or any other type of genetic variant, the detection of which could be beneficial to the subject whose genetic material is to be analyzed.

EXAMPLES

Introduction

Prematurity is more prevalent in African-Americans than European-Americans. We investigated the role of a functional SNP in the promoter of the SERPINH1 gene, enriched among those of African ancestry, and preterm premature rupture of membranes (PPROM), the leading identifiable cause of preterm birth. The SERPINH1 gene encodes Hsp47, a chaperone essential for collagen synthesis. The SERPINH1 −656 minor "T" allele had a greater frequency in African populations and the "T" alle was significantly more frequent in African-Americans than European-Americans (7.4% vs. 4.1%). The −656 "T" allele displayed significantly reduced promoter activity compared to the major −656 "C" allele in amnion fibroblasts, which lay down the fibrillar collagen that gives tensile strength to the amnion. An initial case-control study demonstrated that the −656 "T" allele is significantly more frequent in African-American neonates (P<0.0009) born from pregnancies complicated by PPROM compared to controls (odds ratio of 3.22, 95% CI: 1.50, 7.22). There was no significant difference in ancestry among cases and controls using a dihybrid model based on 29 ancestry-informative markers. Adjusting the results of the case-control study for admixture still yielded a statistically significant association between the −656 "T" allele and PPROM (P<0.002). A follow up case-control study with a second sample gave similar results. The combined case-control findings showed a highly significant (P<0.0000045) association between the −656 "T" allele and PPROM. The SERPINH1 −656 "T" allele is the first example of an ancestry informative marker associated with a pregnancy complication causing preterm birth in African-Americans.

Methods

Study Populations

A number of population samples were used for the estimation of the −656 minor "T" allele frequency. These included European-Americans from State College, Pa. (n=148), Bolivian from La Paz (n=92), Mayans from Guatamala (n=40), Mexicans from Tlapa, Mexico (n=144), South Asian Indians (n=140), Han Chinese (n=43), Benin from Nigeria (n=76), and seven different ethnic groups from Sierra Leone (Creole, n=37; Fula, n=7; Limba, n=23; Loko, n=9; Mandingo, n=8; Mende, n=93, and Temne, n=59). All of these DNA samples were collected with informed consent for biomedical research.

Subjects in the case-control study were African-American women and their neonates receiving obstetrical care at the Hospital of the University of Pennsylvania, Philadelphia, or Hutzel Hospital, Detroit. The study was approved by the respective Institutional Review Boards as well as the Institutional Review Board of the National Institute of Child Health and Human Development, and written informed consent was obtained from mothers before collection of the samples. Control samples (n=358) were obtained from neonates of singleton pregnancies delivered at term of mothers with no prior history of PPROM or preterm labor. Cases of PPROM (n=244) were defined as neonates from pregnancies complicated by rupture of membranes prior to 37 weeks of gestation. The diagnosis of membrane rupture was based on pooling of amniotic fluid in the vagina, amniotic fluid ferning patterns and a positive nitrazine test. Women with multiple gestations, fetal anomalies, trauma, connective tissue diseases and medical complications of pregnancy requiring induction of labor were excluded.

Genotyping

Genomic DNA was extracted from umbilical cords, cord blood, or neonate cheek swabs as previously described (11). The −656 C/T SNP in the SERPINH1 promoter was genotyped using PCR products generated with forward primer 5'-CCACTGTCGCCCAGATTATTTA-3' (SEQ ID NO: 1) and reverse primer 5'-CAGTGCCCTTCTCCATACTTGT-3' (SEQ ID NO: 2) (12). After initial denaturation at 94° C. for 5 min, PCR was performed for 35 cycles of denaturation at 94° C. for 45 s, annealing at 60° C. for 45 s, and extension at 72° C. for 1 min, followed by a final 10 min extension step at 72° C. The 624 bp product was digested with endonuclease ApaL1, which yielded one fragment for the −656 "T" allele and two fragment with sizes of 446 and 178 bp for the −656 "C" allele. The fragments were resolved in 1% agarose gels. MMP1 (10) and MMP8 (11) promoter genotypes were determined as previously reported.

Assessment of Population Structure

Because many African-American populations have substantial admixture which is not evenly distributed throughout the population, there is a chance that some of the observed association could be the result of admixture stratification. To control for admixture stratification, we typed 29 AIMs, which are useful for calculating gene flow between West African and Western European populations (11). These markers were used to calculate the individual biogeographical ancestry (BGA) levels of the persons in the study in the context of the two primary parental populations (West African and Western European) using parental allele frequencies and the maximum likelihood as previously reported (11). These BGA estimates were then used as conditioning variables in the logistic regression analyses to control for any effects that admixture stratification could have on the phenotype. The unadjusted OR for the SERPINH1 genotype and PPROM association was estimated. Next, adjusted OR estimates were computed by incorporating the admixture estimates into the model. The resulting odds ratio is an average of the SERPINH1 genotype, PPROM association, over subjects with like genetic profiles.

Analysis of Linkage Disequilibrium

The Haploview 3.2 program (www.broad.mit.edu/mpg/haploview/) was used to test for linkage disequilibrium. We also evaluated the association among SNPs in the controls and found no significant association between the SERPINH1 and MMP8 genotypes (Fisher exact test, P<0.47).

Construction of Promoter-Reporter Plasmids

To determine whether the −656C/T SNP influences transcription of the SERPINH1 gene, we obtained a 1176 bp fragment from −1104 to +72 bp of the SERPINH1 promoter, amplified using forward and reverse primers with the indicated sequences (forward primer: 5'-CCACTGTCGCCCA-GATTATTTA-3' (SEQ ID NO: 3) reverse primer: 5'-GTCTC-CCGCCCCTCACCT-3' (SEQ ID NO: 4). A mutagenesis kit (Stratagene, Lo Jolla, Calif.) was used to create the targeted alleles with a uniform backbone sequence. Promoter fragments were cloned into the pGL3-Basic vector (Promega, Madison, Wis.), which contains the firefly luciferase gene as a reporter. The DNA sequences of the promoter constructs were confirmed prior to use and three different plasmid preparations for each construct were tested.

Cell Culture and Transfection

Primary cultures of human amnion fibroblasts and human dermal fibroblast cells were cultured in Dulbecco's modified Eagle's medium (DMEM) (10). Human uterine smooth muscle cells were cultured in Smooth Muscle Cell Basal Medium (SmBM) with growth factors as previously described (17). The media were supplemented with 10% fetal bovine serum and antibiotics (100 IU/ml penicillin G, 100 IU/ml streptomycin sulfate, 0.25 µg/ml amphotericin B; Gibco/BRL, Gaithersburg, Md.). All cells were maintained at 37° C. in a water-saturated atmosphere under 5% $CO_2$ in air.

For transfection, $100 \times 10^5$ amnion fibroblasts, $20 \times 10^5$ uterine smooth muscle cells, and $40 \times 10^5$ dermal fibroblasts were seeded in individual wells of a 12-well culture plate. Cells were transfected using FuGENE 6 transfection reagent (Roche, Indianapolis, Ind.) with 0.5 µg of the pGL3 vector containing a 1176 bp SERPINH1 promoter fragment coupled to the firefly luciferase reporter gene. In each transfection, 25 ng pRL-TK (Promega), a control plasmid expressing *Renilla reniformis* luciferase, was used to correct for transfection efficiency. The medium was changed 24 h post-transfection and cultures were continued for an additional 24 h in serum-free medium before collecting cells for the luciferase assays.

Luciferase Assays

After 36-48 h culture, the transfected cells were lysed in lysis buffer and 20 µl aliquots of supernatant were then assayed for luciferase activity using the Dual-Luciferase Reporter Assay System (Promega) as previously described (11). Promoter activities were expressed as the ratio between *Photinus* luciferase and *Renilla* luciferase activities.

Electrophoretic Mobility Shift Assays (EMSA)

Nuclear proteins were extracted as described previously (11). The following double-stranded oligonucleotide probes (SNP identified in bold) were constructed: −656 C sense: 5'-TTCCTTCCTGTGCACTCCTCCAAGC-3' (SEQ ID NO: 5); −656 C antisense: 5'-GCTTGGAGGAGTGCACAG-GAAGGAA-3' (SEQ ID NO: 6); −656 T sense: 5'-TTCCT-TCCTGTGTACTCCTCCAAGC-3' (SEQ ID NO: 7); −656 T antisense: 5'-GCTTGGAGGAGTACACAGGAAGGAA-3' (SEQ ID NO: 8); sense unrelated competitor: 5'-ATGCTGT-GAACCTCAGGGTGCTCG-3' (SEQ ID NO: 9); antisense unrelated competitor: 5'-CGAGCACCCTGAGGTTCA-CAGCAT-3' (SEQ ID NO: 10). The double-stranded synthetic oligonucleotides were labeled with T4 polynucleotide kinase and [$\gamma^{32}$P]-ATP. The EMSA binding reaction was mixed in 1× binding buffer (Promega) with 10 µg of nuclear protein, $1 \times 10^5$ c.p.m of $^{32}$P-labeled double-stranded oligonucleotide probe (1 ng) with or without unlabeled competitor probe in a total volume of 10 µl. Reaction mixtures were incubated at room temperature for 30 min and then subjected to 8% PAGE at 250 V for 4 h. The dried gels were then exposed to X-ray film.

Quantitation of SERPINH1 Nascent Transcripts and mRNA

Trizol Reagent (Invitrogen, Carlsbad, Calif.) was used for total RNA preparation from the freshly frozen human amnion tissue. RNA was DNase-treated with DNA-free reagent (Promega). Total RNA (1-5 µg) was used in 20-40 µl of reverse transcriptase reaction with random hexamers (Roche diagnostics) and Moloney murine-leukemia virus reverse transcriptase (Promega, Madison, Wis.). RT reaction (1 µl 1:10 diluted) was added into 20 µl of real-time PCR. The SYBR green dye (Applied Biosystems) was used for the amplification of cDNA. Reactions were run in triplicate on an Applied Biosystems Prism 7000 Real-Time PCR machine. To measure nascent SERPINH1 transcript levels, total RNA was reversed transcribed using 150 nmol of a SERPINH1-specific primer (5-ACGAAATTCGGTCGGAATACA-3; SEQ ID NO: 11) together with 1.5 mmol of a GAPDH-specific primer (5-TAGAGGCAGGGATGATGTTCTGGA-3; SEQ ID NO: 12). Relative fold changes were calculated by using the standard curve or the DCt method. Primer sets were designed by using PRIMER EXPRESS software (Applied Biosystems, Foster City, Calif.). Primers for mature mRNAs were designed to span exon-exon junction and primers for nascent RNA were designed to be in the next exon and intron. The sequences used were as follow: for SERPINH1 mRNA, forward primer, 5-AACGCCATGTTCTTCAAGCCACACT-3 (SEQ ID NO: 13), reverse, 5-TAGTTGTAGAGGCCTGTC-CGGTGCAT-3 (SEQ ID NO: 14); and for Hsp47 nascent RNA, forward primer, 5-GACGGCGCCCTGCT-3 (SEQ ID NO: 15), reverse, 5-AGCATAAATGAGAGGCAGT-GAAGA-3 (SEQ ID NO: 16). The internal control GAPDH primers were 5-GTATCGTGGAAGGACTCATGACCA-3 (SEQ ID NO: 17) and 5-TAGAGGCAGGGATGATGT-TCTGGA-3 (SEQ ID NO: 18).

Statistics

Tests of association were conducted using Pearson Chi-squared and Fisher's exact tests as needed to account for small sample sizes. Odds ratio estimates and exact binomial confidence intervals were computed using Stata 8.0 (Stata Corp., College Station, Tex.). Dose response modeling was done using logistic regression. Estimates of population attributable risk were calculated as described by Bruzzi et al (18). Significant differences in activities among the different promoter constructs were evaluated using the Tukey-Kramer test with P<0.05 considered as significant.

Results

In a study of ethnic/racial distribution, we found that the SERPINH1 −656 "T" allele was most frequent in African populations, particularly those living in Sierra Leone (Table 1). Moreover, the −656 "T" allele was found in greater frequency in African-Americans (n=323) than European-Americans (n=148) (12.4% vs. 4.1%, P<0.024). These observations confirm the higher "T" allele frequency among those with African ancestry.

TABLE 1

Ethnic Distribution of the −656 minor "T" allele in the SERPINH1 gene

| Country (Ethnic Group) | Tested Samples | "T" allele frequency |
| --- | --- | --- |
| Caucasian | 148 | 0.041 |
| Bolivian | 92 | 0.046 |
| Guatemala (Mayan) | 40 | 0.075 |
| Mexican | 144 | 0.056 |
| South Asian | 140 | 0.046 |
| Chinese | 43 | 0.083 |
| Nigeria | 76 | 0.11 |
| Sierra Leone (Creole) | 37 | 0.24 |
| Sierra Leone (Fula) | 7 | 0.21 |
| Sierra Leone (limba) | 23 | 0.24 |
| Sierra Leone (Loko) | 9 | 0.17 |
| Sierra Leone (Mandigo) | 8 | 0.125 |
| Sierra Leone (Mende) | 93 | 0.13 |
| Sierra Leone (Temne) | 59 | 0.25 |

To determine the ancestry of the SERPINH1 alleles, panels of DNA from well-characterized populations was genotyped. The analysis indicates that the SERPINH1 −656 "T" allele is more common in African populations compared to South America (Bolivia, Guatemala, Mexico) and Asia (China). Western European populations have a −656 "T" allele frequency of 0.041.

Figure 2B:
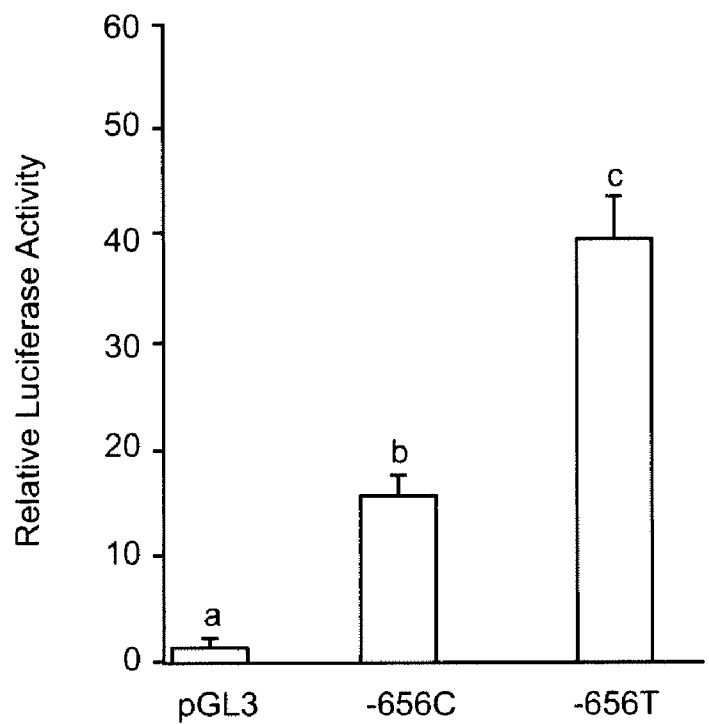
Figure 2C:
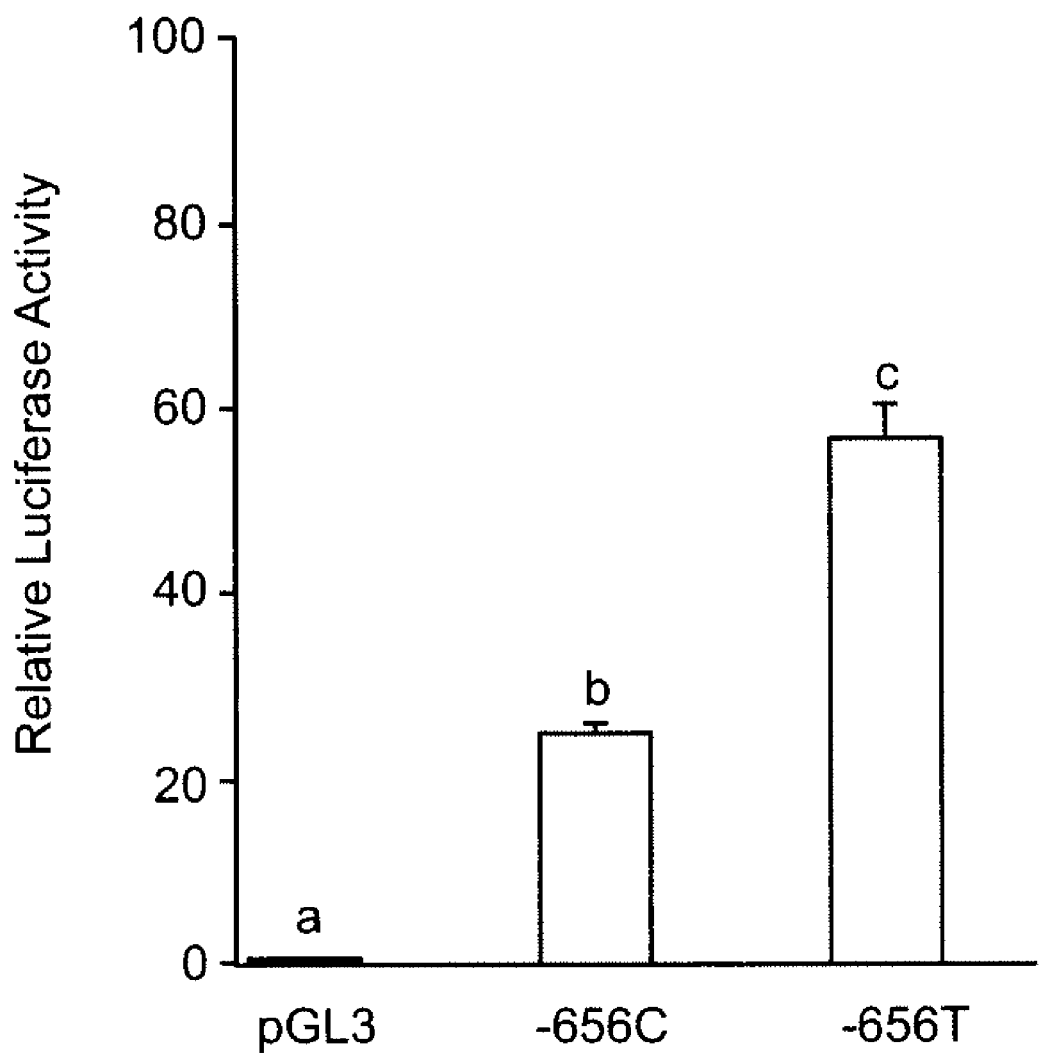

We next performed promoter function studies comparing the activities of the two −656 alleles, which revealed host cell-specific differences between the minor "T" and major "C" alleles (FIG. 2). The minor "T" allele displayed significantly reduced promoter activity in amnion fibroblasts, which lay down the fibrillar collagen of the amnion. In contrast, the activity of the minor "T" allele promoter was significantly greater than that of the major "C" allele in the context of dermal fibroblasts and uterine smooth muscle cells. These findings raised the possibility that fetuses that inherit the SERPINH1 −656 "T" allele might be at greater risk for preterm birth due to PPROM because of a reduced amnion collagen synthesis and consequently, reduced tensile strength.

Measurement of nascent SERPINH1 RNA and mRNA from amnion samples with a −656 C/C and −656 C/T genotype by real time PCR revealed significantly lower quantities of both nascent transcripts, a reflection of transcription rate, and mRNA in the amnion samples with a −656 C/T genotype (Table 2). This result is consistent with the notion that in vivo, the −656 "T" allele has reduced promoter activity.

TABLE 2

In Vivo Expression of SERPINH1 in Amion is Dependent on −656 Genotype

|  | −656 C/C | −656 C/T | P Value |
|---|---|---|---|
| Nascent transcripts | 3.42 + 0.70 (6) | 0.56 + 0.16 (4) | <0.02 |
| mRNA | 31.91 + 0.47 (6) | 7.41 + 1.33 (4) | <0.01 |

Quantitative PCR analysis of nascent and mature SERPINH1 RNAs in human amnion tissue.
Values are means ± S.E.
Numbers in parentheses indicate the number of samples analyzed.

Figures 3A, 3B, 3C:
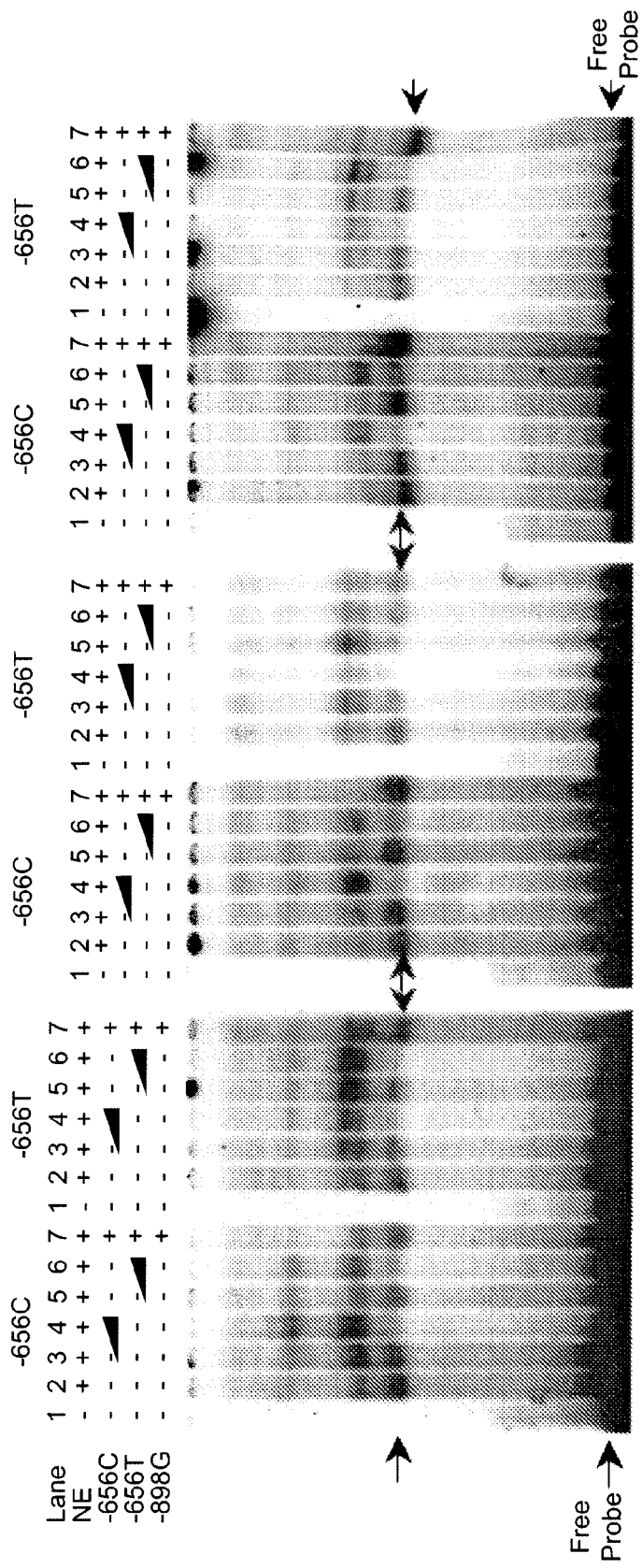
FIG. 3A-C. The −656 region specifically binds a nuclear protein. EMSA studies were performed with nuclear extracts prepared from A, amnion fibroblasts, B, dermal fibroblasts, and C, uterine smooth muscle cells, and $^{32}$P-labeled double strand oligonucleotides representing the −656 "C" and "T" alleles. Specific binding was established by addition of increasing amounts of unlabeled double strand oligonucleotide representing the two SERPINH1 alleles or a irrelevant nucleotide sequence. Arrowheads indicate specific complexes and free probe.

Electrophoretic mobility shift assays (EMSA) revealed a specific complex formed with nuclear extracts from the three different cells types with oligonucleotides representing the −656 "C" and "T" alleles (FIG. 3). The minor "T" allele oligonucleotide probe had lower affinity for the nuclear proteins in dermal fibroblasts and uterine smooth muscle cells, but equivalent affinity to the major "C" allele oligonucleotide in amnion fibroblasts. Despite the significant differences in promoter activities among the three cell types, there were no clear differences in the gel shift patterns. This suggests that either post-translational modifications or association of transcriptional co-activators or co-repressors with the nuclear factor binding to the −656 region explains the differential activities of the two promoter alleles in different cell types.

To determine if the SERPINH1 −656 minor "T" allele contributes to risk of PPROM, we performed an initial case-control study in African-Americans. The study focused on the genotype of the offspring based on the hypothesis that the genotype of the extraembryonic tissues (fetal membranes) represents the primary determinant of risk of PPROM. Analysis of the demographic characteristics of the controls (n=174), neonates born at term from normal pregnancies, and the cases (n=152), neonates from pregnancies complicated by PPROM revealed no significant differences in maternal age, gravidity and parity. However, the length of gestation (controls: 39.1±1.3 (SD) weeks; cases: 31.9±2.8, P<0.0001) and birth weight (controls: 3,309±483 gm; cases: 1,937±502, P<0.0001) were significantly lower in the PPROM group, as expected.

The minor SERPINH1 −656 "T" allele was found significantly more frequently in African-American (11.51% allele frequency, P<0.0009) in pregnancies complicated by PPROM compared to controls (4.05%) with an odds ratio of 3.22 (95% CI: 1.50, 7.22). There was a statistically significant allele dose effect for the −656 "T" allele in a test for trend (P<0.002) with respect to risk of PPROM. Heterozygotes for the "T" allele had an odds ratio of 2.68 (95% CI 1.45, 4.95) for PPROM compared to homozygotes for the common "C" allele, and homozygotes for the "T" allele had yet an additionally greater risk with an odds ratio of 2.68 compared to heterozygotes for the "T" allele.

The urban African-American population from which our subjects were drawn is heterogeneous, and this heterogeneity could have confounded the findings of the association study as a result of population stratification. Consequently, we performed analyses using 29 ancestry informative markers (AIMs) to determine if population stratification could have affected our findings. There was no significant difference in ancestry among cases and controls using a dihybrid model (% African ancestry: cases, 0.840±0.135 (SD); controls, 0.831±0.144, P=0.571). Moreover, using logistic regression analysis we adjusted the results of the case-control study for admixture and still observed a statistically significant association between the minor −656 "T" allele and PPROM (P<0.002, and an odds ratio of 3.14, 95% CI 1.53, 4.47). The population attributable risk for the unadjusted data was 12% (95% CI 3.6%, 19.9%) and 12.3% (95% CI 5.2%, 20.6%) for the admixture-adjusted data. A second case-control study was conducted on a different sample of 184 controls and 92 cases. This demonstrated again that there was a significant association of PPROM with neonates carrying the −656 "T" allele (−656 "T" allele frequency: cases: 11.41%, controls: 5.16%, P<0.0076; odds ratio: 2.37, 95% CI: 1.17, 4.79). Combing the two case-control studies (cases=244; controls=358) we obtained a highly significant association between the −656 "T" allele and PPROM (−656 "T" allele frequency: cases: 11.48%, control: 4.47%; P<0.0000045, odds ratio: 2.77, 95% CI: 1.73, 4.95).

In previous studies, associations between SNPs in the promoters of the MMP1 (10) and MMP8 (11) genes and PPROM were reported. These genes encoding matrix metalloproteinases, are located on chromosome 11q approximately 27 megabases away from the SERPINH1 gene, raising the theoretical possibility that linkage disequilibrium between the MMP alleles and the −656 "T" allele accounted for of findings. We determined the MMP1 genotypes and MMP8 haplotypes of the samples analyzed in this study SNP and utilized the Haploview 3.2 program to test for linkage disequilibrium with the −656 SERPINH1 SNP. There was no evidence for linkage disequilibrium between the SERPINH1 SNP and the MMP1 and MMP8 alleles (P>0.47), although the previously described linkage disequilibrium within the MMP8 haplotype (+17C/G and −799C/T) was confirmed.

Discussion

We have found that a SNP in the promoter of the SERPINH1 gene, which reduces promoter function in amnion fibroblast cells, is strongly associated with risk of PPROM, the leading identifiable cause of preterm birth. Amnion samples carrying the −656 "T" allele have reduced amounts of nascent SERPINH1 transcripts and mRNA, which would result in reduced Hsp47 protein and consequently reduced interstitial collagen synthesis and a weaker amnion, more prone to rupture. The −656 "T" allele is enriched in individuals of African ancestry. Our use of a panel of AIMs to assess population structure argues against the possibility that population stratification confounded our analysis. Thus, it appears that the SERPINH1 −656 "T" allele or a gene in linkage disequilibrium with it represents a significant risk factor for preterm birth in African-Americans. To the best of our knowledge this is the first example of an ancestry informative marker that is associated with a pregnancy complication causing preterm birth.

The cell-host specific differential activities of the −656 C/T SERPINH1 promoter genotypes is also of interest in that the minor "T" allele which displayed lower activity in amnion fibroblasts compared to the major "C" allele, displayed higher activity in dermal fibroblasts and uterine smooth muscle cells. Since both keloids, a fibrotic response in skin, and uterine fibroid tumors, which have a dense collagen matrix, are more prevalent in African-Americans, it is intriguing to speculate that a single SNP could contribute to multiple phenotypes (15, 16).

REFERENCES FOR EXAMPLE 1

1. Kempe, A., Wise, P. H., Barkan, S. E., Sappenfield, W. M., Sachs, B., Gortmaker, S. L., Sobol, A. M., First, L. R., Pursley, D., Rinehart, H. & et al. (1992) N Engl J Med 327, 969-973.
2. Ahern, J., Pickett, K. E., Selvin, S. & Abrams, B. (2003) J Epidemiol Community Health 57, 606-611.
3. Meis, P. J., Goldenberg, R. L., Mercer, B. M., Iams, J. D., Moawad, A. H., Miodovnik, M., Menard, M. K., Caritis, S. N., Thurnau, G. R., Dombrowski, M. P., Das, A., Roberts, J. M. & McNellis, D. (2000) Am J Perinatol 17, 41-45.
4. Wang, X., Zuckerman, B., Pearson, C., Kaufman, G., Chen, C., Wang, G., Niu, T., Wise, P. H., Bauchner, H. & Xu, X. (2002) JAMA 287, 195-202.
5. Macones, G. A., Parry, S., Elkousy, M., Clothier, B., Ural, S. H. & Strauss, J. F., 3rd (2004) Am J Obstet Gynecol 190, 1504-1508.
6. Winkvist, A., Mogren, I. & Hogberg, U. (1998) Int J Epidemiol 27, 248-254.
7. Carr-Hill, R. A. & Hall, M. H. (1985) Br J Obstet Gynaecol 92, 921-928.
8. Parry, S. & Strauss, J. F., 3rd (1998) N Engl J Med 338, 663-670.
9. Ferrand, P. E., Parry, S., Sammel, M., Macones, G. A., Kuivaniemi, H., Romero, R. & Strauss, J. F., 3rd (2002) Mol Hum Reprod 8, 494-501.
10. Fujimoto, T., Parry, S., Urbanek, M., Sammel, M., Macones, G., Kuivaniemi, H., Romero, R. & Strauss, J. F., 3rd (2002) J Biol Chem 277, 6296-6302.
11. Wang, H., Parry, S., Macones, G., Sammel, M. D., Ferrand, P. E., Kuivaniemi, H., Tromp, G., Halder, I., Shriver, M. D., Romero, R. & Strauss, J. F., 3rd (2004) Hum Mol Genet. 13, 2659-2669.
12. Rocnik, E. F., van der Veer, E., Cao, H., Hegele, R. A. & Pickering, J. G. (2002) J Biol Chem 277, 38571-38578.
13. Skinner, S. J., Campos, G. A. & Liggins, G. C. (1981) Obstet Gynecol 57, 487-489.
14. Hampson, V., Liu, D., Billett, E. & Kirk, S. (1997) Br J Obstet Gynaecol 104, 1087-1091.
15. Marshall, L. M., Spiegelman, D., Barbieri, R. L., Goldman, M. B., Manson, J. E., Colditz, G. A., Willett, W. C. & Hunter, D. J. (1997) Obstet Gynecol 90, 967-973.
16. Taylor, S. C. (2003) Cutis 71, 271-275.
17. Leite, R. S., Brown, A. G. & Strauss, J. F., 3rd (2004) FASEB J 18, 1418-1420.
18. Bruzzi, P., Green, S. B., Byar, D. P., Brinton, L. A. & Schairer, C. (1985) Am J Epidemiol 122, 904-914.

Abbreviations: PPROM, preterm premature rupture of membranes; Hsp47, heat shock protein 47; EMSA, electrophoretic mobility shift assays; AIMs, ancestry informative markers; BGA, biogeographical ancestry.

Example 2

A Functional 12 bp Deletion in the Promoter of the SERPINH1 Gene Protects Against Preterm Rupture of Membranes Further investigations of the promoter region of the SERPINH1 gene revealed that a 12 bp deletion in the promoter of the SERPINH1 gene (−694 to −683: 5'-cac ctt gct cag-3') also contributes to the risk of PPROM. When the 12 bp deletion is present, the risk of PPROM is lowered. In other words, the effect of the deletion is opposite to that of the presence of T at −656. In fact, the unfavorable increase in the risk of PPROM caused by T at −656 is overcome by the concomitant presence of the 12 bp deletion, i.e. an individual with a genotype of T at −656 and a 12 bp deletion at −694 to −683 does not have an elevated risk of PPROM, compared to individuals with a C at position −656.

Material and Methods

Study Populations.

Subjects in the case-control study were African-American women and their neonates receiving obstetrical care at the Hospital of the University of Pennsylvania or Hutzel Hospital. A written informed consent was obtained from mothers before collection of the samples. The study was approved by the respective institutional review boards. 403 control samples were obtained from neonates of singleton pregnancies delivered at term of mothers with no prior history of PPROM or preterm labor. 291 case samples were collected from neonates from pregnancies complicated by rupture of membranes before 37 weeks of gestation. The diagnosis of membrane rupture was based on pooling of amniotic fluid in the vagina, amniotic fluid ferning patterns, and a positive nitrazine test. Women with multiple gestations, fetal anomalies, trauma, connective tissue diseases, and medical complications of pregnancy requiring induction of labor were excluded from the study.

Genotype

Genomic DNA was extracted from umbilical cords, cord blood, or neonate cheek swabs using traditional methods as previously described (Wang, human molecular genetics). The 12 bp+/− polymorphism in the SERPINH1 promoter was genotyped by using PCR products generated with forward primer 5'-aag gga aca gag gcc cag aaa ggg aaa gta-3' (SEQ ID NO: 20) and reverse primer 5'-taa tag agg cag aga tgc ctg ggg aac tt-3' (SEQ ID NO: 21). After the hot start of denaturation at 94° C. for 5 min, amplification was carried out for 35 cycles of 94° C., 30 sec; 60° C., 30 sec and 72° C., 45 sec, followed by a 5 min final extension at 72° C. Since the functional −656C/T SNP is 19 bp away from the 12 bp+/− polymorphism, the PCR amplification covers both of the above polymorphisms. When the amplification contains 12 bp+ the product was 144 bp; with the 12 bp deletion, the product was 132 bp. The −656C/T genotype was determined using endonuclease ApaL I digestion as previously reported (Wang, H. et al., 2006), which produced two fragments of 57 bp and 87 bp for the major −656C allele. The 12 bp deletion is consistently accompanied by the −656T allele. The final digested fragments can be resolved and identified on a 12% acrylamide gel.

Population Stratification

Because African-Americans are not an isolated population, there is a chance that some of the observed association could be a result of admixture stratification. To evaluate the possible effects of population stratification, 29 ancestry-informative markers were used to calculate the individual biogeographical ancestry levels of the persons in the study in the context of the two primary parental populations (West African and Western European) as previously reported (Wang et al, *Human Mol. Genet.*). The assessment of the studied population structure shows no significant difference in the genetic profiles between PPROM cases and the controls (p>0.05).

Plasmid Construction for Promoter Function Test

To determine whether the 12 bp+/− polymorphism influences or confounds with the functional −656C/T SNP in the transcription of the SERPINH1 gene, a previously constructed 1176 bp plasmid containing the SERPINH1 promoter from −1104 to +72 with −656C/T SNP was used as the backbone of a newly constructed plasmid DNA (Wang, H. et al., 2006). The QuickChange mutagenesis kit (Stratagene, USA) was used to create the allele of a 12 bp deletion. The vector is the pGL3-Basic vector (Promega, USA) which contains the firefly luciferase gene as a reporter. The plasmid construction was confirmed by DNA sequencing. Three different plasmid preparations for each targeted construction were tested.

Cell Culture and Transfection

DMEM media was used to culture the primary cultures of human amnion fibroblasts cells. The media was supplemented with 10% FBS and antibiotics [100 units/ml penicillin G, 100 units/ml Streptomycin sulfate, and 0.25 µg/ml amphotericin B (Gibco/BRL, Gaithersburg, Md.)]. All cells were maintained at 37° C. in a water-saturated atmosphere under 5% $CO_2$ in air.

$100 \times 10^5$ amnion fibroblast cells were seeded in each well of a 12-well culture plate for the next day's transfection (in 16-18 hours). Fugene 6 transfection reagent (Roche Diagnostics, Indianapolis, Ind.) with 0.5 µg empty pGL3-Basic vector (negative controls) or 0.5 µg target plasmid coupled to the firefly luciferase reporter gene was used as instructed by the manual for cells in each well. In each transfection, 25 ng of pRL-TK (Promega), a control plasmid expressing *Renilla reniformis* Luciferase, was used to correct for transfection efficiency. The transfection medium, was changed with serum-free culture medium (no treatment) or serum-free culture medium supplemented with 10 nM all-trans retinoic acid (at RA) to enhance the transfection efficiency in 18-24 hours. The transfected cells were maintained for an additional 36 hours before the next luciferase assays.

Luciferase Assays

The Dual-Luciferase Reporter Assay System (Promega) was used for the luciferase activity assays after 36-48 hours culture of the transfected cells. The cells were lysed and we took 20 µl aliquots of the supernatant for the luciferase activity assay as previously described (Wang, H. et al., 2004). Promoter activities were expressed as the ratio between *Photinus* luciferase and *Renilla* luciferase activities.

Statistics

Significant differences of activities among promoter constructions were evaluated using the Tukey-Krammer test with p<0.05 considered as significant. Tests of association were conducted using Pearson's X2 test and Fisher's exact test as needed to account for small sample sizes. Odds ratio estimated and exact binomial confidence intervals were computed by using Stata 8,0 (Stata, college Station, T X).

Results

Promoter Activity of the SERPINH1 Gene with 12 bp+/− Polymorphism

Promoter function studies comparing the activities of the two 12 bp+/12 bp− (−694 to −683: 5'-cac ctt get cag-3' SEQ ID NO: 22) alleles were performed. The minor "12 bp−" allele displayed significantly increased promoter activity in amnion fibroblasts, which lay down the fibrillar collagen of the amnion, regardless of whether or not the other functional SNP at −656 in the same promoter is C or T allele. These findings raise the possibility that fetuses that inherit the SERPINH1 "12 bp−" allele might be at reduced risk for preterm birth due to its protective effect against PPROM because of an increased amnion collagen content.

Association Study Between PPROM and SERPINH1 Promoter with 12 bp Deletion (Genetic)

To determine if the SERPINHI 12 bp+/12 bp− polymorphism is associated with a risk of PPROM, a case-control study in African-Americans was performed. The study focused on the genotype of the offspring based on the hypothesis that the genotype of the extraembryonic tissues (fetal membranes) represents the primary determinant of risk of PPROM. Analysis of the demographic characteristics of the controls (neonates born at term from normal pregnancies, N=403), and the cases of neonate from pregnancies complicated by PPROM (N=291), revealed no significant differences in maternal age, gravidity and parity. However, the length of gestation (controls: 39.3±1.2 (SD) weeks; cases: 31.8±2.9, p<0.0001) and birth weight (controls: 3,308±485 gms; cases: 1,934±500, p<0.0001) were significantly lower in the PPROM group, as expected.

The frequency of the minor SERPINH1 "12 bp−" allele was found to be significantly different in pregnancies complicated by PPROM (0% allele frequency, P=0.0124) compared to controls (2.23%) with an odds ratio of 0 (95% CI: 0, 0.5806). The SERPINH1 "12 bp" insertion/deletion polymorphism is located in the promoter region at −683 to −694 bp from the transcription start site. Thus, the locus of the "12 bp" polymorphism is only 19 bp away from the −656C/T SNP described in Example 1. All the identified 12 bp deletions are consistently accompanied with −656T.

Since the urban African-American population from which our subjects were drawn is heterogeneous, analyses were performed using 29 ancestry informative markers to determine if population stratification could have affected the findings. The results showed that there was not significant difference in ancestry among cases and controls using a dihybrid model (Wang et al., 2006).

TABLE 3

| Ethnic distribution | | |
|---|---|---|
| Ethnic group (country) | No. of tested samples | 12 bp deletion frequency |
| Caucasian | 148 | 0.014 |
| Bolivian | 92 | 0.04 |
| Mayan (Guatemala) | 40 | 0.04 |
| Mexican | 144 | 0.05 |
| South Asian | 140 | 0.04 |
| Chinese | 43 | 0.06 |
| Nigerian | 76 | 0.01 |
| Creole (Sierra Leone) | 37 | 0.00 |
| Fula (Sierra Leone) | 7 | 0.00 |
| Limba (Sierra Leone) | 23 | 0.00 |
| Loko (Sierra Leone) | 9 | 0.00 |
| Mandigo (Sierra Leone) | 8 | 0.00 |
| Mende (Sierra Leone) | 93 | 0.06 |
| Temne (Sierra Leone) | 59 | 0.22 |

REFERENCES FOR EXAMPLE 2

Wang, H., Parry, S., Macones, G., Sammel, M. D., Ferrand, P. E., Kuivaniemi, H., Tromp, G., Halder, I., Shriver, M. D., Romero, R. & Strauss, J. F., m (2004) Functionally significant SNP MMP8 promoter haplotypes and preterm premature rupture of membranes. Hum. Mol. Genet. 13, 2659-2669.

Wang, H., Parry, S., Macones, G., Sammel, M., Kuivaniemi, H., Tromp G., Halder, I., Shriver, M., Romero, R., & Strauss, J. F. III (2006) A Functional SNP in the Promoter of the SERPINH1 Gene Encoding Hsp47 Increases Risk of Preterm Premature Rupture of Membranes and Preterm Birth in African-Americans. Proc Natl Acad Sci USA 103 (36): 13463-13467.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for predicting a risk of preterm delivery in a human subject, comprising the steps of:
   a) determining, in one or more nucleic acid samples from said subject,
      i) the presence of a C or T at a single nucleotide polymorphism (SNP) at position −656 of a SERPINHI gene promoter; and
      ii) whether a 12-base pair (SEQ ID NO: 22) sequence is present or deleted at positions −694 to −683 of said SERPINH1 gene promoter; and
   b) predicting an increased risk of preterm delivery in the human subject if a T is detected at position −656 and the 12 base pair sequence (SEQ ID NO: 22) is detected at position −694 to −683 in said SERPINHI gene promoter, as compared to a human subject where a T is detected at position −656 and the 12 base pair (SEQ ID NO: 22) deletion is detected at positions −694 to −683 in said SERPINH1 gene promoter; and wherein said SNP at position −656 and said 12 base pair deletion at positions −694 to −683 in said SERPINHI gene promoter modulate the level of transcription of the SERPINH 1 gene.

2. The method of claim 1, wherein said one or more nucleic acid samples is a maternal DNA sample or a paternal DNA sample, or both.

3. The method of claim 1, wherein said one or more nucleic acid samples is a fetal DNA sample.

4. The method of claim 1, further comprising the step of providing therapeutic intervention to a human female predicted to be at increased risk of preterm delivery, wherein said therapeutic intervention is selected from the group consisting of lifestyle changes, dietary modifications, and providing vitamin C dietary supplements.

* * * * *

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 1
ccactgtcgc ccagattatt ta                                      22

<210> SEQ ID NO 2
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 2
cagtgccctt ctccatactt gt                                      22

<210> SEQ ID NO 3
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 3
ccactgtcgc ccagattatt ta                                      22

<210> SEQ ID NO 4
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 4
gtctcccgcc cctcacct                                           18

<210> SEQ ID NO 5
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 5
ttccttcctg tgcactcctc caagc                                   25

<210> SEQ ID NO 6
```

-continued

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 6
gcttggagga gtgcacagga aggaa                                           25

<210> SEQ ID NO 7
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 7
ttccttcctg tgtactcctc caagc                                           25

<210> SEQ ID NO 8
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 8
gcttggagga gtacacagga aggaa                                           25

<210> SEQ ID NO 9
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 9
atgctgtgaa cctcagggtg ctcg                                            24

<210> SEQ ID NO 10
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 10
cgagcagggt gaggttcaca gcat                                            24

<210> SEQ ID NO 11
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 11
acgaaattcg gtcggaatac a                                               21

<210> SEQ ID NO 12
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 12
```

-continued tagaggcagg gatgatgttc tgga                                                24

<210> SEQ ID NO 13
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 13
aacgccatgt tcttcaagcc acact                                               25

<210> SEQ ID NO 14
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 14
tagttgtaga ggcctgtccg gtgcat                                              26

<210> SEQ ID NO 15
<211> LENGTH: 14
<212> TYPE: DNA
<213> ORGANISM: Artificial
<220> FEATURE:
<223> OTHER INFORMATION: synthetic oligonucleotide primer

<400> SEQUENCE: 15
gacggcgccc tgct                                                           14

<210> SEQ ID NO 16
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 16
agcataaatg agaggcagtg aaga                                                24

<210> SEQ ID NO 17
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 17
gtatcgtgga aggactcatg acca                                                24

<210> SEQ ID NO 18
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 18
tagaggcagg gatgatgttc tgga                                                24

<210> SEQ ID NO 19
<211> LENGTH: 1375
<212> TYPE: DNA

<213> ORGANISM: Homo sapiens

<400> SEQUENCE: 19

| | | | | |
|---|---|---|---|---|
| accaccacca | ggcttcccca | caaccactaa | cagagggcag | ggacccaggt gattgactca | 60 |
| tttgctgggt | actgggattt | ttttgctccc | caggatccag | gcaagcacct agaagaaaga | 120 |
| agatactcaa | tgcattcatt | catgactgaa | tgaatgaaga | gtccctaccc tgtcccttcc | 180 |
| tctccatact | gcgtccatcc | aatagctatc | attaaactac | taaagaggac ttttcggagg | 240 |
| gtagggagcc | tcggctgatc | agaaattgag | ccactgtcgc | ccagattatt tagggtttcc | 300 |
| taaataatct | gcctcactga | atcactgaat | tccctactaa | caggtacata ccccacagat | 360 |
| ggacatcgca | cagggcaagg | actttgttca | gctctcagct | gtgtcctcag cacctagaac | 420 |
| agtaatgaat | accctagctt | aacttggagg | tcaaggagct | atcagtttgc gagggtgggg | 480 |
| taggaattga | cagtgagacc | tgaggcctgt | gggaggggac | ccaaagaggg aggggatgca | 540 |
| atagggaggg | ggccagggt  | gacaaggatt | gaggaaggga | gagaggggggg aaaaaaagca | 600 |
| agggatgcct | tagaaccaca | tttcacagcc | aagggaacag | aggcccagaa agggaaagta | 660 |
| acctgcttag | ggtcacacag | caccttgctc | agtggagagc | caggttttcc ttcctgtgca | 720 |
| ctcctccaag | cccagccaga | ccacctgaag | ttccccaggc | atctctgcct ctattactcc | 780 |
| acgacttgaa | ctttccgggt | gccgggcagg | taccgggtct | ggtctgctcc ctctccctct | 840 |
| ggccatcgct | gaggttgagg | tttttgaat  | gtacaagtat | ggagaagggc actgccttca | 900 |
| gaagcctgaa | cgtctcccct | gagagggagg | gggtgcacag | gactcaattg tttcagcttg | 960 |
| aaaatggggg | agagcgggga | gaaggggaga | tggctctgct | tggggcagag cccctgcggg | 1020 |
| gaaagggggcg | cctgaaagga | cgtgcgattc | ggagtgggct | agcttatgca gagagcctgg | 1080 |
| gggtgggagg | aagctcgcac | tctgaaggac | acgctgatcc | ccgtggggac tcccggcgcc | 1140 |
| ccgcagcccg | ggccgccgag | ggaggcagta | ggacccaggg | gccgggaggc gccggcagag | 1200 |
| ggaggggccg | ggggccgggg | aggttttgag | ggaggtcttt | ggcttttttt ggcggagctg | 1260 |
| gggcgccctc | cggaagcgtt | tccaactttc | cagaagtttc | tcgggacggg caggaggggg | 1320 |
| tggggactgc | catatataga | tcccgggagc | aggggagcgg | gctaagagta gaatc | 1375 |

<210> SEQ ID NO 20
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 20
aagggaacag aggcccagaa agggaaagta                                          30

<210> SEQ ID NO 21
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 21
taatagaggc agagatgcct ggggaactt                                           29

<210> SEQ ID NO 22
<211> LENGTH: 12

```
<212> TYPE: DNA
<213> ORGANISM: Homo sapiens

<400> SEQUENCE: 22
caccttgctc ag                                                              12
```